(12) United States Patent
Puagazhenthi et al.

(10) Patent No.: US 9,916,419 B2
(45) Date of Patent: Mar. 13, 2018

(54) PROCESSING ELECTRONIC DOCUMENTS

(71) Applicants: Pavithra Puagazhenthi, Bangalore (IN); Chandrashekara Rangapura Shettappa, Bengaluru (IN)

(72) Inventors: Pavithra Puagazhenthi, Bangalore (IN); Chandrashekara Rangapura Shettappa, Bengaluru (IN)

(73) Assignee: Siemens Aktiengesellschaft, München (DE)

( * ) Notice: Subject to any disclaimer, the term of this patent is extended or adjusted under 35 U.S.C. 154(b) by 119 days.

(21) Appl. No.: 15/040,917

(22) Filed: Feb. 10, 2016

(65) Prior Publication Data
US 2016/0232297 A1  Aug. 11, 2016

(30) Foreign Application Priority Data

Feb. 10, 2015  (IN) .............................. 165/KOL/2015

(51) Int. Cl.
*G06F 17/30* (2006.01)
*G06F 19/00* (2018.01)

(52) U.S. Cl.
CPC ...... *G06F 19/321* (2013.01); *G06F 17/30011* (2013.01); *G06F 17/30268* (2013.01)

(58) Field of Classification Search
CPC ......... G06F 17/30011; G06F 17/30014; G06F 17/30265; G06F 17/30268; G06F 19/321; G06F 19/322; G06F 19/324; G06F 19/325; G06F 19/326; G06Q 50/24
See application file for complete search history.

(56) References Cited

U.S. PATENT DOCUMENTS

| | | | |
|---|---|---|---|
| 6,396,941 B1 * | 5/2002 | Bacus et al. .................. | 382/128 |
| 7,536,644 B2 | 5/2009 | Fowkes et al. ............... | 715/720 |
| 2003/0210281 A1 * | 11/2003 | Ellis et al. ..................... | 345/838 |
| 2007/0016686 A1 | 1/2007 | Hollebeek et al. ........... | 709/238 |
| 2007/0043744 A1 * | 2/2007 | Carro .......................... | 707/100 |
| 2011/0161854 A1 * | 6/2011 | Shukla ......................... | 715/771 |
| 2014/0250109 A1 * | 9/2014 | Wang et al. ........ G06F 17/3053 |  |
| | | | 707/723 |
| 2016/0203165 A1 * | 7/2016 | Tanikawa et al. ........................ |  |
| | | | G06F 17/30268 |
| | | | 707/769 |

* cited by examiner

*Primary Examiner* — Andrew W Johns
(74) *Attorney, Agent, or Firm* — Lempia Summerfield Katz LLC (57) ABSTRACT

A method and a system for processing electronic documents are provided. The method includes displaying a first image. The first image includes one or more portions. The one or more portions are associated with metadata. A first portion of the one or more portions of the first image is selected. Upon selection of the first portion, at least one subsequent image is displayed based on a first selection. The subsequent images also include one or more portions associated with metadata. One or more subsequent portions of the at least one subsequent image is selected. Upon selecting the portions of the first image and the subsequent image, one or more electronic documents corresponding to the selections are retrieved.

20 Claims, 7 Drawing Sheets

PROCESSING ELECTRONIC DOCUMENTS

This application claims the benefit of IN 165/KOL/2015, filed on Feb. 10, 2015, which is hereby incorporated by reference in its entirety.

BACKGROUND

The present embodiments relate to processing electronic documents. Electronic documents in the medical domain such as electronic health documents (EHR) and Electronic Medical Documents (EMR) are maintained in hospitals and clinics in order to document the medical history of the patients undergoing various therapies and treatments. For example, the EHR includes patient data such as, for example, medications, vital statistics, medical history, laboratory data and diagnostic reports. There is a vast amount of data that may prove useful to the physicians.

Sometimes, due to the numerous categories of data available, the physicians may encounter difficulty while searching for the required reports. In some instances, the physician may want to mine for reports that deal with a certain clinical condition. In this case, the physician will have to manually read through EHRs of the patients and shortlist the reports that include the clinical condition. This method of searching consumes a lot of time and is not efficient. Further, the physician may have to deal with getting the spellings right for keyword based search. Some clinical conditions have very difficult spellings that prompt the physician to search for the right spelling and enter the right word in the search field. This may be time consuming and frustrating for the physician.

SUMMARY AND DESCRIPTION

The scope of the present invention is defined solely by the appended claims and is not affected to any degree by the statements within this summary.

An efficient method to search medical documents for a particular clinical condition is to be provided. A search method where the physician need not know the right spelling for the clinical conditions is also to be provided. The physician is able to filter EHRs based on human physiology rather than keyword based search.

The present embodiments may obviate one or more of the drawbacks or limitations in the related art. For example, a method and system for processing electronic documents based on graphical representation are provided. As another example, the physicians are allowed to filter electronic documents based on a clinical condition.

A method and system for filtering electronic documents based on graphical representation includes displaying a first image. The first image includes one or more portions. The one or more portions of the image are associated with metadata. The image may be a still image or an animate image. In one embodiment, the image is a generic human body structure. The one or more portions of the image may represent different features of the image. For example, if the image is a human physiological structure, then the portions of the image represent a physiological feature (e.g., head or heart) of the image. The one or more portions of the first image are associated with metadata. The metadata includes, for example, a keyword string, an index number, a hash tag and the like.

Further, the method includes selecting a first portion of the one or more portions of the first image. The first portion of the image may be selected using an input such as, for example, a mouse click, a touch input, or a gesture input. Thereafter, at least one subsequent image is displayed based on a first selection. The at least one subsequent image includes one or more portions. The one or more portions of the subsequent image are associated with metadata, similar to the metadata associated with the portions of the first image. Subsequently, the method involves selecting one or more subsequent portions of the at least one subsequent image. In an embodiment, more than one subsequent image is displayed based on the number of subsequent selections. Thereafter, one or more electronic documents are retrieved corresponding to at least one of the first selection and the at least one subsequent selection.

According to an aspect, the one or more portions of the first image represent at least one part of a human body. The first image represents a human physiological structure. The first image is segmented into a number of portions. The portions of the first image represent a specific physiological entity of the human body. For example, a portion may represent a head portion of the human body figurine, and another portion may represent the chest portion of the human body shown in the first image.

In another aspect, the subsequent images represent an image associated with the first selection. For example, if the first selection was a heart portion of the human body, the subsequent images represent the details of the heart portion like the left ventricle, aorta and the like. The subsequent images may be displayed based on the subsequent selections.

In yet another aspect, each portion of the one or more portions of the first image and the at least one subsequent image is associated with metadata. The metadata includes a hash tag, a keyword phrase, an index numeral, other metadata, or any combination thereof. The metadata associated with the portions of the image facilitates in retrieving one or more electronic documents.

In a variant, the one or more portions of the first image and the subsequent images are generated by integrating a grid structure. The grid structure includes a plurality of polygonal structures, which are superimposed on the images to render the one or more portions on the image. The grid structure enables a user to select one or more portions of the image, as required.

The metadata associated with the selected portion is used to retrieve electronic documents. When one or more portions of the image are selected, the metadata associated with the portion is extracted and a query is generated. Based on the query, electronic documents are retrieved from a database or a repository.

In yet another variation, the metadata provides a relationship between the selected portion of the image and the electronic documents that are retrieved. For example, if a user selects a head portion in the image, then the metadata includes information that aids in retrieving electronic documents that are related to clinical conditions related to the head of patients. In an instance, when the user selects a heart portion in the image, metadata associated with the heart portion of the image may include a keyword string as heart. Thereafter, the keyword string in the metadata is extracted, and the electronic documents regarding heart related conditions are retrieved.

In a further variant, multiple selections of a plurality of portions of the image are received. For example, a user may select a heart portion and a lung portion of the image simultaneously in order to retrieve electronic documents associated with heart and lung conditions. In this case, the metadata of the selected portions are used to retrieve the relevant electronic documents.

In an embodiment, the one or more electronic documents are selected from a plurality of electronic documents based on the selected portion of the image. The plurality of electronic documents is stored in a database server. The metadata associated with the selected portion of the image is used to query the electronic documents stored in the database server.

In yet another embodiment, the electronic document is a patient document, a health document, a medical report, a diagnostic report, a diagnostic image, or any combination thereof. In some embodiments, the electronic documents may include other articles such as technical papers and journals.

In still yet another embodiment, the metadata is a hash tag, a keyword phrase, an index numeral, other metadata, or any combination thereof. The metadata associated with one or more portions of the image provides relationship between a selected portion and the electronic documents retrieved.

A system for processing electronic documents is provided. The system includes a processor and a memory coupled to the processor. The memory includes an image augmentation module configured to render an image. The image includes one or more portions. The memory includes an event detection module configured to receive a selection event. The selection event includes selection of at least a portion of the image. The event detection module is configured to detect one or more types of inputs such as, for example, a keystroke, a mouse click, a touch input, and a gesture input. The event detection module is configured to detect several simultaneous selection events. For example, the event detection module may detect two or more portions of the image, which may be selected simultaneously. The memory includes an image sequencing module configured to provide a subsequent image based on the selection event. The image sequencing module provides a subsequent image based on the selected portion of the first image. The image sequencing module provides a further image based on a portion of the subsequent image that is selected. Further, the memory includes a retrieval module configured to retrieve one or more electronic documents corresponding to one or more selection events.

In an embodiment, the image augmentation module is configured to assign metadata to the at least one portion of the image. The image augmentation module assigns metadata to the at least one portion of the image based on the features of the portion. For example, if the portion represents a chest portion of the human body, metadata is assigned such that the metadata facilitates in retrieving all chest related electronic documents from a database.

In another embodiment, the image augmentation module is configured to integrate a grid structure with the image. In order to divide the image into a plurality of portions, the image augmentation module is configured to integrate a grid structure with the image. The grid structure divides the image into a plurality of portions, and each portion is associated with metadata. The user may select a portion of the image based on the demarcation provided by the grid structure.

In yet another embodiment, the subsequent image provided by the image sequencing module replaces a previous image rendered by the image augmentation module. For example, if a portion of a heart image is selected, the heart image is replaced by a detailed view of the selected portion.

In still yet another embodiment, the event detection module is configured to receive one or more selections of the one or more portions of the image. For example, the user may select multiple portions of the image. Based on the multiple selections, the keywords associated with the multiple selections are extracted and the corresponding electronic documents are retrieved.

In an aspect, the retrieval module is configured to generate a keyword string based in the metadata associated with the selection event. For example, when the user selects one or more portions of the image, the metadata associated with the portion of the image is extracted and concatenated to form a search query. The search query is used to retrieve electronic documents from the database.

In another aspect, the retrieval module is configured to retrieve one or more electronic documents based on the metadata associated with the selection event. The metadata associated with one or more portions of the image selected during the selection event are extracted, and a search query is generated. The search query is sent to the database server to retrieve one or more electronic documents associated with the search query.

In another variation, the retrieval module is configured to generate keyword strings based on the metadata associated with at least a portion of the image and a dictionary archive. The dictionary archive includes one or more words associated with the metadata extracted from the selected portion of the image. The words in the dictionary archive may be used to generate an effective search query to retrieve the most relevant electronic documents from the database.

In yet another variation, one or more electronic documents are stored in a database. The database may be located at a same location or a remote location with respect to the machine querying the electronic documents. Further, the database may be a database server using a relational database management system.

DETAILED DESCRIPTION

Various embodiments are described with reference to the drawings, wherein like reference numerals are used to refer like elements throughout. In the following description, for the purpose of explanation, numerous specific details are set forth in order to provide thorough understanding of one or more embodiments. Such embodiments may be practiced without these specific details.

Figure 1:
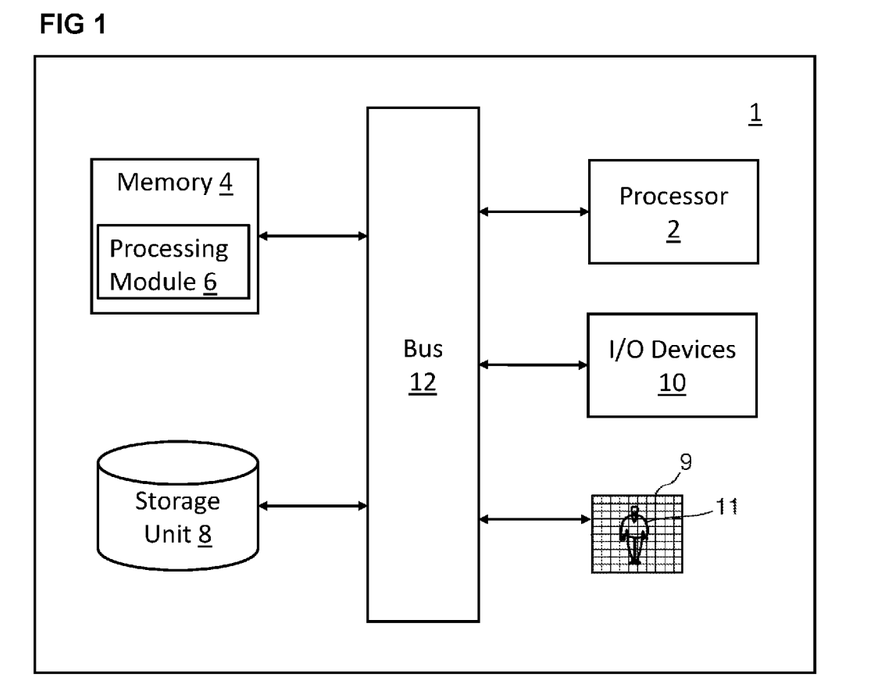
FIG. 1 illustrates an exemplary computing device capable of processing electronic documents.

FIG. 1 illustrates an exemplary computing device 1 capable of processing electronic documents. The computing device 1 may be a personal computer, a laptop computer, a server computer, a tablet and the like. In FIG. 1, the computing device 1 includes a processor 2, a memory 4, a storage unit 8, a display 9, and input/output devices 10 connected to each other through a bus 12.

The processor 2, as used herein, may be any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, or any other type of processing circuit. The processor 2 may also include embedded controllers, such as generic or programmable logic devices or arrays, application specific integrated circuits, single-chip computers, and the like.

The memory 4 may be volatile memory and non-volatile memory. A variety of computer-readable storage media may be stored in and accessed from the memory 4. The memory 4 may include any suitable elements for storing data and machine-readable instructions, such as read only memory, random access memory, erasable programmable read only memory, electrically erasable programmable read only memory, hard drive, removable media drive for handling compact disks, digital video disks, diskettes, magnetic tape cartridges, memory cards, and the like. As depicted, the memory 4 includes an electronic document processing module 6 for filtering electronic documents based on a graphical menu, according to one or more embodiments described above.

The electronic documents processing module 6 may be stored in the form of machine computer readable instructions on any of the aforementioned storage media (e.g., non-transitory computer-readable storage media) and may be executed by the processor 2. For example, when the electronic documents processing module 6 is executed by the processor 2, the machine readable instructions cause the processor to display a first image. The first image includes one or more portions. The one or more portions of the first image are associated with metadata. The machine readable instructions cause the processor 2 to receive a selection event. The selection event includes selection of at least one portion of the first image. Upon receiving the first selection, the machine readable instructions cause the processor 2 to provide a subsequent image based on the selection event. Upon receiving the first selection and one or more subsequent selections, the machine readable instructions cause the processor to retrieve one or more electronic documents corresponding to one or more selection events.

The storage unit 8 may be a non-transitory storage medium configured for storing files and databases. For example, the storage unit 8 includes electronic documents such as an electronic patient document, an electronic health document, an electronic medical report, a diagnostic report and a diagnostic image. The storage unit 8 may be located at a remote location and may be accessed via a network connection.

The display 9 may include an LED monitor, an LCD monitor, a CRT monitor, a touch screen display, an OLED display, and the like. The display 9 is configured to display images such as image 11. The image 11 may be an image of human physiology having one or more portions. Further, the display 9 is operable to accept one or more inputs such as a keystroke, a mouse click, a gesture input and a touch input.

The input/output devices 10 may include a keyboard, a keypad, a touch sensitive display screen, a mouse, and the like. The input device/output devices 10 enable the user to interface with the computing device 1 for filtering electronic document based on a graphical menu. For example, the display 9 may display a graphical image divided into a plurality of portions. Thereafter, the user may select at least a portion of the image using an input such as, a keystroke, a touch input, or a gesture input. Upon receiving the input, the display 9 may display a subsequent image based on the first input. When the user is done with the selection process, the electronic documents that are retrieved are displayed in the monitor.

Figure 2:
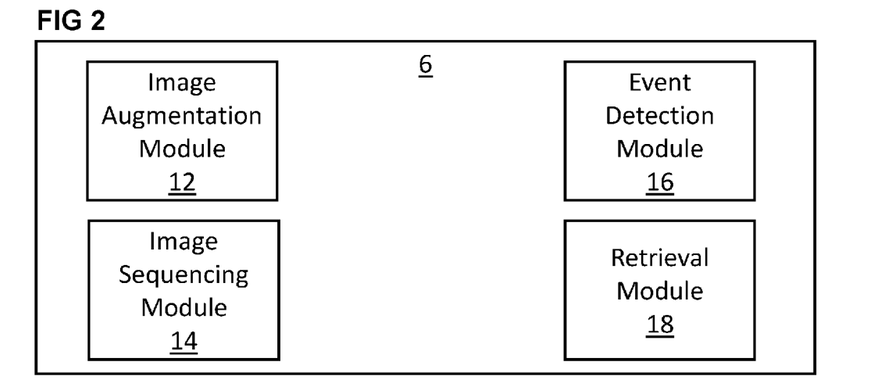
FIG. 2 illustrates an exemplary block diagram of the electronic document processing module, according to an embodiment.

FIG. 2 illustrates an exemplary block diagram of the electronic document processing module 6. The electronic document processing module 6 includes an image augmentation module 12, an image sequencing module 14, an event detection module 16, and a retrieval module 18. The image augmentation module 12 renders an image and integrates a grid structure with the image in order to divide the image into multiple portions. In some embodiments, the grid structure may not be used, and the image may be divided using one or more contours. Further, the image augmentation module associates one or more metadata to the one or more portions of the image. The metadata may be related to a particular portion of the image. The metadata may include an index number, a keyword string, a hash tag, or any combination thereof. The event detection module 14 receives one or more selection events performed by the user. The selection events may be a mouse click, a keystroke, a touch input, a gesture input, or any combination thereof. Based on the selection events, the image sequencing module 16 provides subsequent images to the user. Thereafter, the user may perform one or more subsequent selection events. Based on the one or more selection events, the retrieval module 18 retrieves one or more electronic documents. In an embodiment, the retrieval module 18 extracts the metadata associated with the selected portions of the images. Thereafter, the retrieval module 18 may assemble the metadata into a search query. The search query may be sent to a database server storing the electronic documents to retrieve relevant electronic documents. In an exemplary embodiment, the retrieval module 18 uses a dictionary archive for generating the search query. The dictionary archive may include a plurality of domain specific synonyms for a given word. For example, for a metadata that denotes heart, the dictionary archive may have one or more synonyms used in the medical/clinical terminology (e.g., angio, cardio and the like). In an exemplary embodiment, the retrieval module 18 may retrieve the electronic documents from a remote database server.

Figure 3:
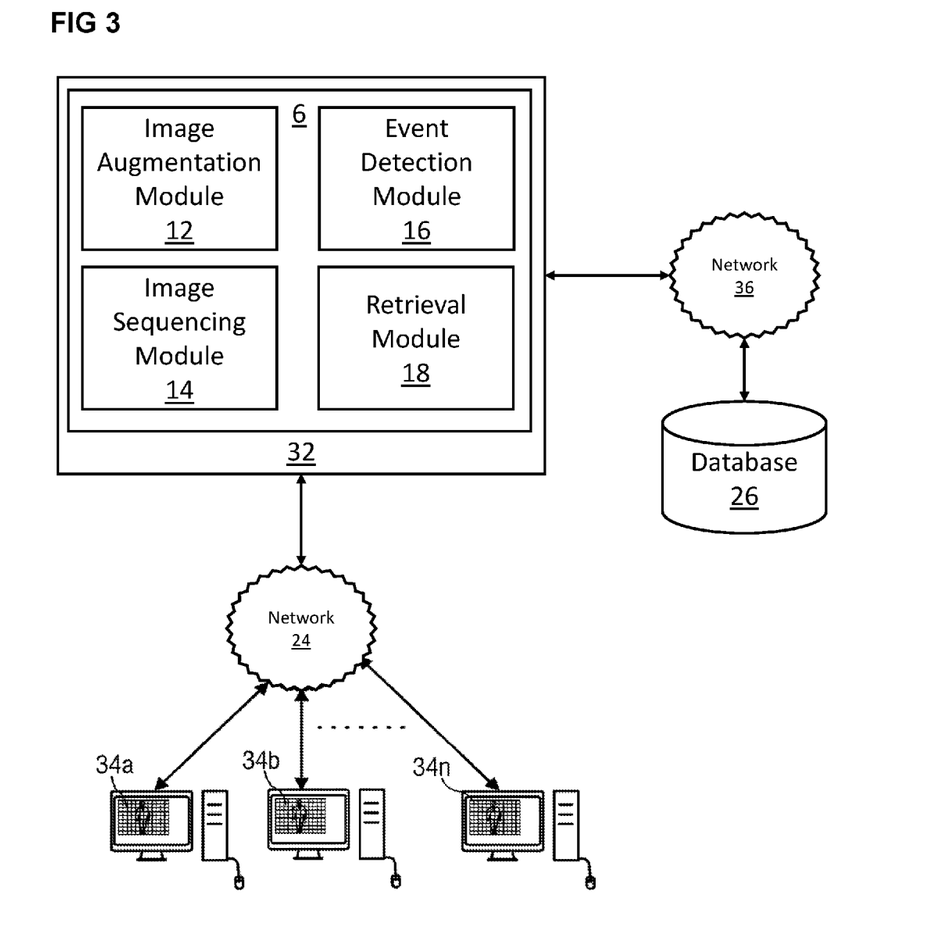
FIG. 3 illustrates an exemplary block diagram of the system for processing electronic documents, according to an embodiment.

FIG. 3 illustrates an exemplary block diagram of the system for processing electronic documents, according to an embodiment. The system includes a server 32, networks 24 and 36, one or more client devices 34a-34n, and a database 26. The server 32 includes an image augmentation module 12, an event detection module 14, an image sequencing module 16, and a retrieval module 18. The server 32 serves the one or more client devices 34a-34n connected through the network 24. The client devices 34a-34n may be computing devices such as workstations, desktop computers, laptops, tablets, and the like. The network 24 may be a LAN, a Wireless LAN, a Metropolitan Area network, Wi-Fi, a Bluetooth network, or any combination thereof. The server 32 is connected to a database 26 though the network 36. The database includes one or more electronic documents that are retrieved by the server 32.

In an embodiment, the image augmentation module 12 in the server 32 is configured to render an image. The image includes one or more portions. The image augmentation module may render a first image, such as an image 11, (e.g., a human physiology) on the display 9 of one or more client devices 34a-34n. The image augmentation module integrates a grid structure with the first image to divide the first image into one or more portions. The image augmentation module associates one or more metadata to the portions of the first image. The metadata will be used to retrieve one or more electronic documents from the database 26.

In another embodiment, the event detection module 14 in the server 32 is configured to receive a selection event. The selection event includes selection of at least a portion of the image. The selection event is performed by a user using a mouse click, a touch input, a keystroke, a gesture input, another input, or any combination thereof.

Based on the selection events, the image sequencing module 16 is configured to provide a subsequent image. In an embodiment, a subsequent image may be a detailed image of the portion of the first image that is selected. For example, if the portion of the first image is a heart portion, then the subsequent image is a detailed image of the heart that is again divided into a number of portions. The user may select a portion of the heart. Upon a subsequent selection, the image sequencing module 16 provides a detailed image of the portion selected by the user.

When the user is done with selection process, the retrieval module 18 is configured to retrieve one or more electronic documents corresponding to the selection events. In an embodiment, the retrieval module extracts one or more metadata associated with the one or more selected portions of the images. The metadata is processed into a search query that is forwarded to the database 26 for retrieving one or more relevant electronic documents. The server 32 may be connected to the database 26 though the network 36. The server 32 may be accessing the database 26, which is remotely located via the network 36.

Figure 4A:
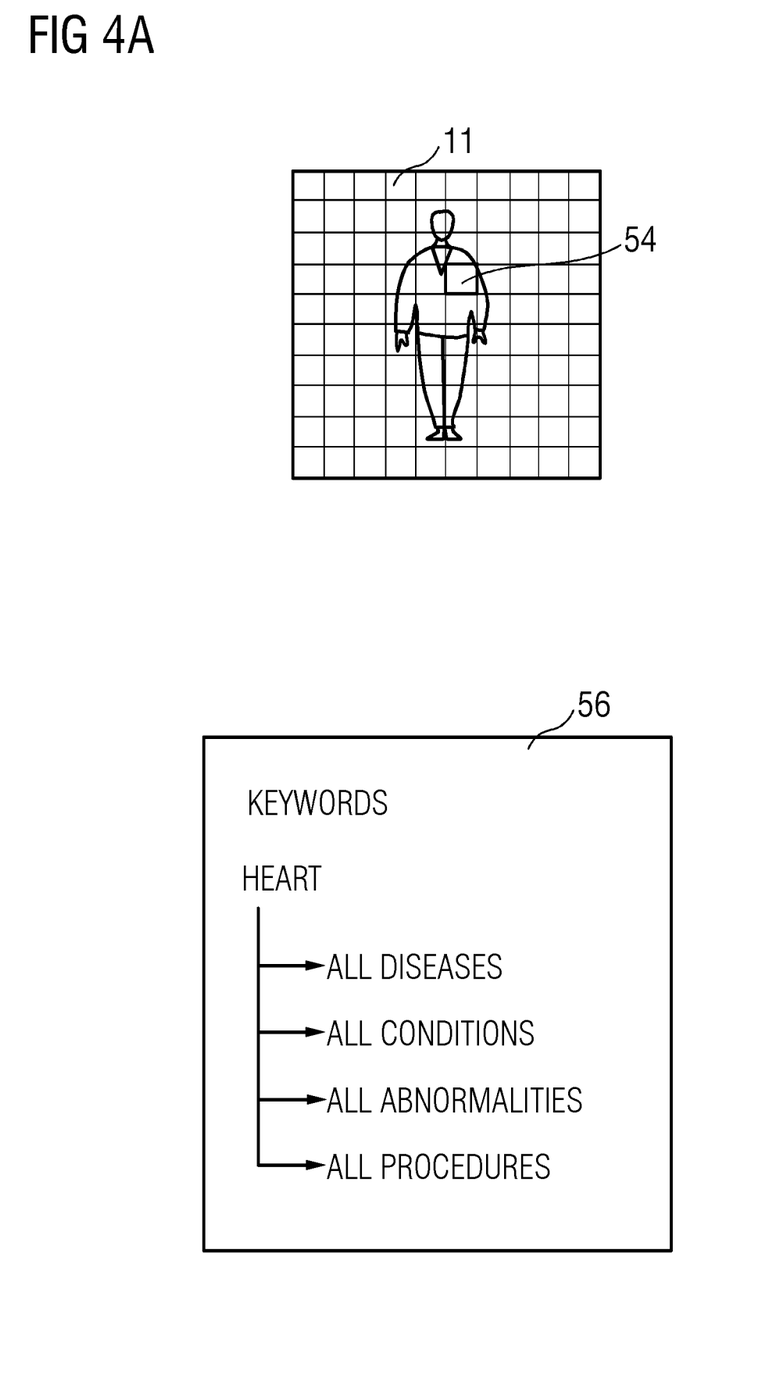
FIG. 4A illustrates an exemplary image displayed to a user for enabling the user to perform a first selection for filtering electronic documents.

FIG. 4A illustrates an exemplary image displayed to the user for enabling the user to select a portion of the image, according to an embodiment. The image 11 is displayed on the display 9. The image augmentation module integrates a grid structure with the image 11, as shown in FIG. 4A. The user may select a portion 54 of the image 11, as shown in FIG. 4A. The portion 54 is associated with metadata that characterizes the portion. In this case, the metadata indicates a heart portion. Based on the selection, a keyword table 56 is generated by the retrieval module 18. Based on the keyword table 54, the electronic documents related to heart, such as documents related to diseases, conditions, abnormalities and procedures associated with the heart may be retrieved, in case the selection is finalized by the user.

Figure 4B:
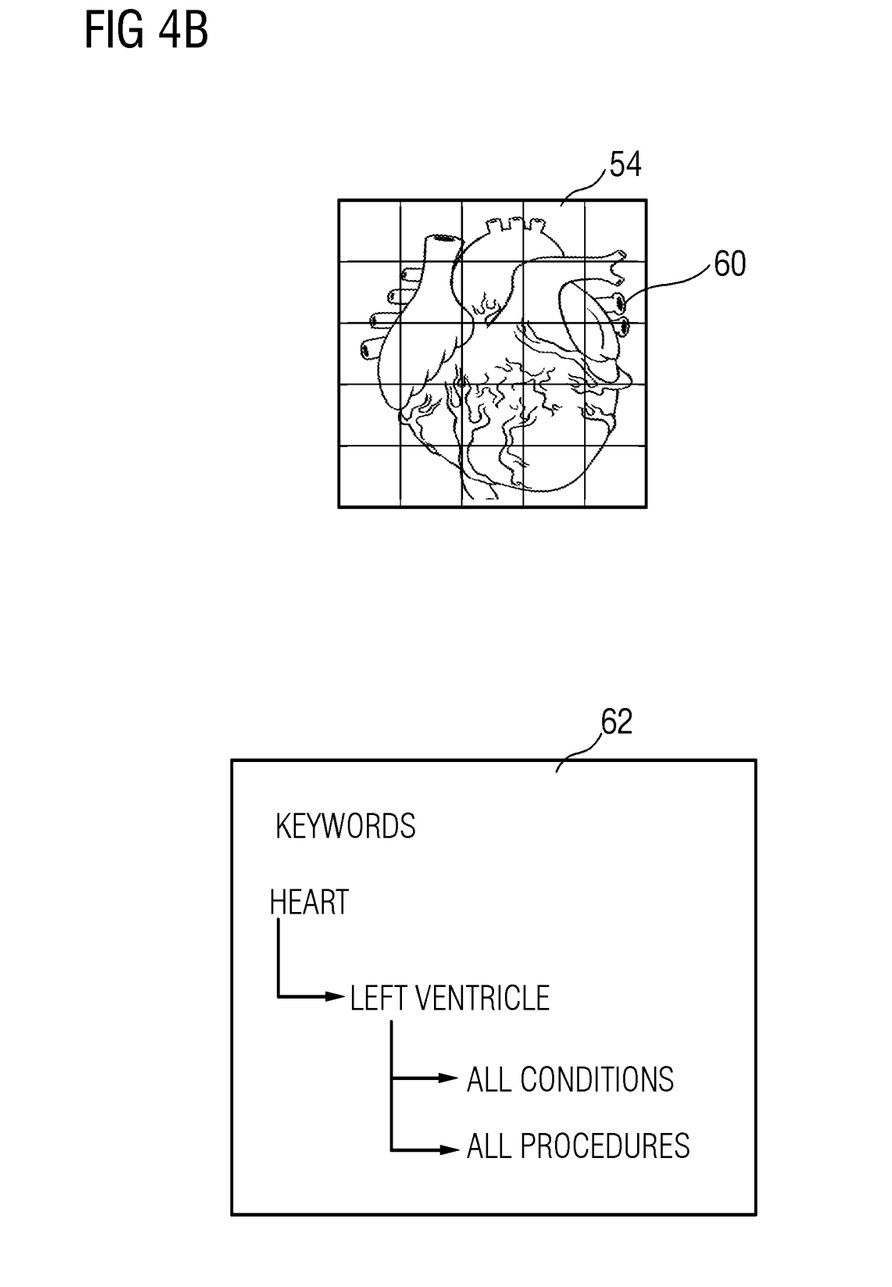
FIG. 4B illustrates an exemplary subsequent image displayed after the first selection event by the user.

FIG. 4B illustrates an exemplary image displayed after the first selection event by the user. The selected portion 54 is now displayed in detail to the user. In FIG. 4B, the heart portion selected in image 11 is replaced with a subsequent image 54 of the heart. The subsequent image 54 is a detailed version of the heart clearly depicting the physiology of the heart. Further, the subsequent image 54 of the heart is divided into multiple portions by the image augmentation module 12. The user may select a portion of the subsequent image 54 by performing a subsequent selection event. In this case, the user selects a second subsequent portion 60, which represents the left ventricle of the heart. Upon selection of the subsequent portion 60, the retrieval module updates the keyword table 62 to include all the clinical conditions, diseases, and procedures performed on the left ventricle.

Figure 4C:
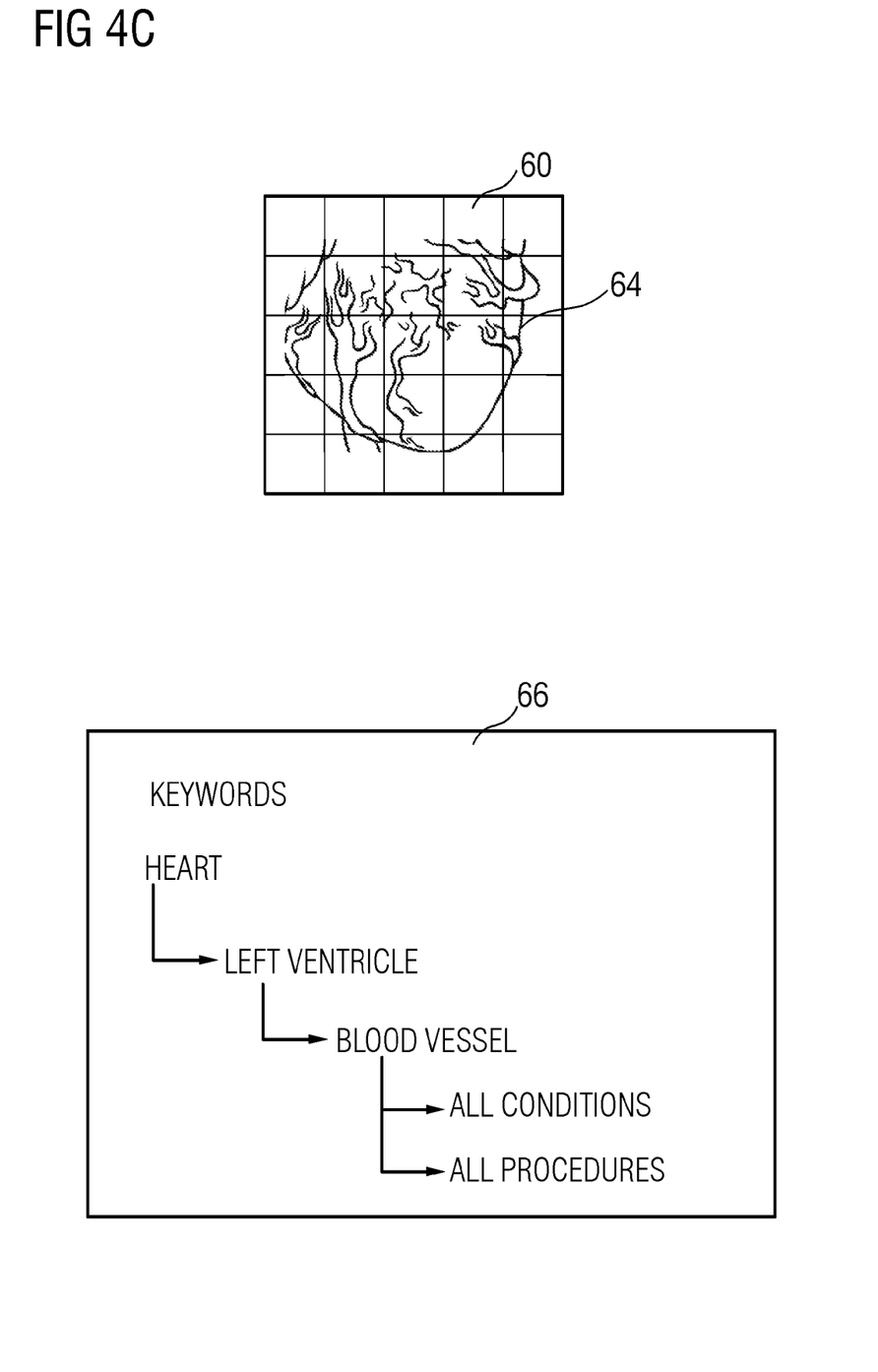
FIG. 4C illustrates an exemplary second subsequent selection of a portion of the image in order the filter the electronic documents.

FIG. 4C illustrates an exemplary second subsequent selection of a portion of the image in order to filter the electronic documents. In FIG. 4C, the image 60 illustrates a detailed diagram of the left ventricle. Thereafter, the second subsequent selection 64 is performed by the user. In this case, a blood vessel on the left ventricle is selected. Based on the second subsequent selection 64, the keyword table 66 is updated to include all the clinical conditions, diseases and procedures associated with the blood vessel.

Figure 4D:
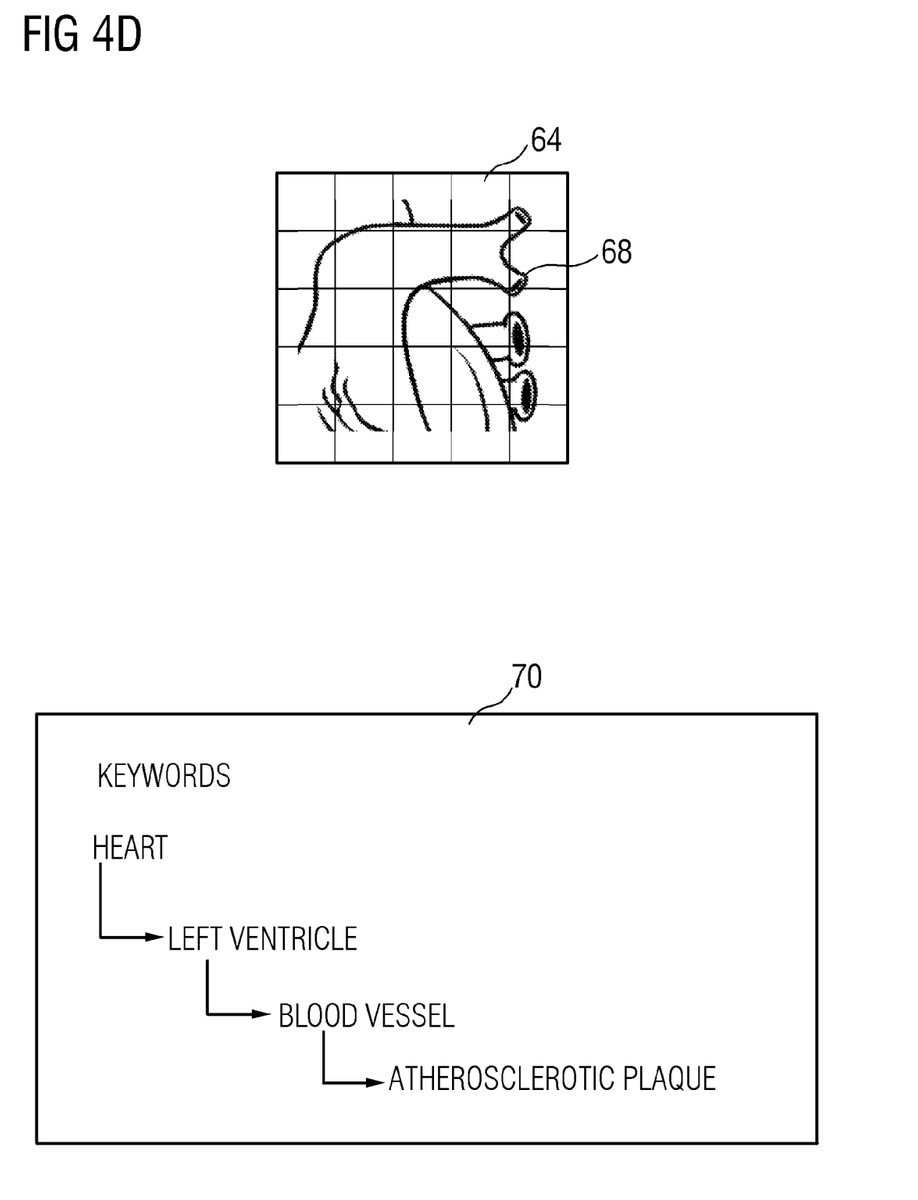
FIG. 4D illustrates an exemplary third subsequent selection of a portion of the image in order to filter the electronic documents.

FIG. 4D illustrates a third exemplary subsequent selection of a portion of the image in order to filter the electronic documents. As shown in FIG. 4D, the user selects atherosclerotic plaque as the third and final selection event. In an embodiment, the final selection may be selected from a drop down list of clinical conditions or procedures. In another embodiment, the final selection may be typed in by the user. Further, the final selection may be ascertained by inputting a selection such as an OK button or SEARCH button provided in the Graphical User Interface (GUI) on the display 9. Subsequently, the keyword table is updated to include all the procedures and conditions associated with atherosclerotic plaque of the blood vessels of the left ventricle of the heart. Upon completing the final selection by the user, one or more records are retrieved from the database and are displayed on the display (e.g., display 9). Further, the user may use the records, as required.

Figure 5:
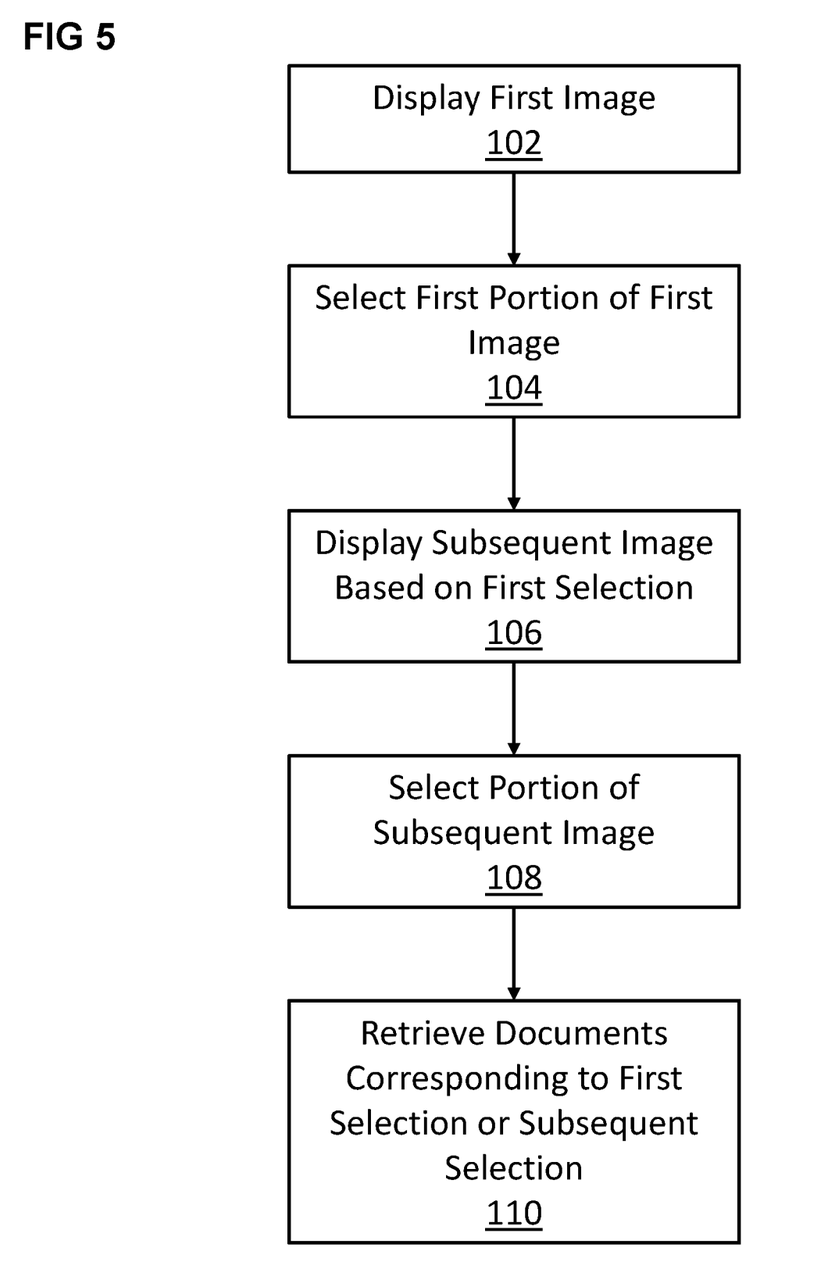
FIG. 5 illustrates exemplary method acts for processing electronic documents, in accordance with an embodiment.

FIG. 5 illustrates exemplary method acts for processing electronic documents. At act 102, a first image is displayed. The first image includes one or more portions that are associated with metadata. The image may be a still image or an animated image. In one embodiment, the image is a generic human body structure. The one or more portions of the image may represent different features of the image. For example, if the image is a human physiological structure, then the portions of the image represent a physiological feature (e.g., head or heart) of the image. The one or more portions of the first image are associated with metadata. The metadata includes for example, a keyword string, an index number, a hash tag, and the like.

At act 104, a first portion of the one or more portions of the first image is selected. The first portion of the image may be selected using an input such as, for example, a mouse click, a keystroke, a touch input, or a gesture input. Thereafter, at least one subsequent image is displayed based on a first selection. The at least one subsequent image includes one or more portions. The one or more portions of the subsequent image are associated with metadata, similar to the metadata associated with the portions of the first image.

At act 106, at least one subsequent image is displayed based on a first selection. The at least one subsequent image includes one or more portions. The one or more portions of the at least one subsequent image are associated with metadata.

At act 108, one or more portions of the at least one subsequent image are selected. In an embodiment, more than one subsequent image is displayed based on the number of subsequent selections.

At act 110, one or more electronic documents corresponding to the first selection, the at least one subsequent selection, or a combination thereof is retrieved. The electronic documents are retrieved from a database server, such as server 26, which may be remotely located.

In an embodiment, the one or more portions of the first image represent at least one part of a human body. The first image represents a human physiological structure. The first image is segmented into a number of portions. The portions of the first image represent a specific physiological entity of the human body. For example, a portion may represent a head portion of the human body figurine, and another portion may represent the chest portion of the human body shown in the first image.

In another embodiment, the subsequent images represent an image associated with the first selection. For example, if the first selection was a heart portion of the human body, the subsequent images represent the details of the heart portion like the left ventricle, aorta and the like. The subsequent images may be displayed based on the subsequent selections.

In yet another embodiment, each portion of the one or more portions of the first image and the at least one subsequent image is associated with metadata. The metadata includes a hash tag, a keyword phrase, an index numeral, other metadata, or any combination thereof. The metadata associated with the portions of the image facilitates in retrieving one or more electronic documents.

In a variant, the one or more portions of the first image and the subsequent images are generated by integrating a grid structure. The grid structure includes a plurality of polygonal structures, which are superimposed on the images to render the one or more portions on the image. The grid structure enables a user to select one or more portions of the image, as required.

In yet another variation, the metadata provides a relationship between the selected portion of the image and the electronic documents that are retrieved. For example, if a user selects a head portion in the image, then the metadata includes information that aids in retrieving electronic documents that are related to clinical conditions related to the head of patients. In an instance, when the user selects a heart portion in the image, metadata associated with the heart portion of the image may include a keyword string as heart. Thereafter, the keyword string in the metadata is extracted, and the electronic documents regarding heart related conditions are retrieved.

The method and system described herein enables a user to retrieve one or more electronic documents based on graphical filtering. The user may save a lot of time and effort that is needed for a keyword based search. Further, the electronic documents extracted will be according to the requirement of the user. The user need not know the spellings of the abnormalities or the procedures that are to be searched. Further, the method and system enable intuitive searching and retrieving of electronic documents.

The present embodiments may take a form of a computer program product including program modules accessible from computer-usable or computer-readable medium storing program code for use by or in connection with one or more computers, processors, or instruction execution system. For the purpose of this description, a computer-usable or computer-readable medium may be any apparatus that may contain, store, communicate, propagate, or transport the program for use by or in connection with the instruction execution system, apparatus, or device. The medium may be an electronic, magnetic, optical, electromagnetic, infrared, or semiconductor system (or apparatus or device), or propagation mediums in and of themselves as signal carriers that are not included in the definition of physical computer-readable medium include a semiconductor or solid state memory, magnetic tape, a removable computer diskette, random access memory (RAM), a read only memory (ROM), a rigid magnetic disk, and optical disk such as compact disk read-only memory (CD-ROM), compact disk read/write, and DVD. Both processors and program code for implementing each aspect of the technology may be centralized or distributed (or a combination thereof) as known to those skilled in the art.

While the present invention has been described in detail with reference to certain embodiments, the present invention is not limited to those embodiments. In view of the present disclosure, many modifications and variations would be presented to those skilled in the art without departing from the scope of the various embodiments of the present invention, as described herein. The scope of the present invention is, therefore, indicated by the following claims rather than by the foregoing description. All changes, modifications, and variations coming within the meaning and range of equivalency of the claims are to be considered within their scope.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of processing electronic documents, the method comprising:
    displaying a first image, wherein the first image includes one or more portions, wherein the one or more portions are associated with metadata;
    selecting a first portion of the one or more portions of the first image;
    displaying at least one subsequent image based on a first selection, wherein the at least one subsequent image includes one or more portions, wherein the one or more portions of the at least one subsequent image is associated with metadata;
    selecting one or more subsequent portions of the at least one subsequent image; and
    retrieving one or more electronic documents corresponding to at least one of the first selection and the at least one subsequent selection.

2. The method of claim 1, wherein the first selection represents at least one part of a human body.

3. The method of claim 1, wherein the at least one subsequent image includes an image associated with the first selection.

4. The method of claim 1, wherein each portion of the one or more portions of the first image and the at least one subsequent image is associated with metadata.

5. The method of claim 1, wherein the one or more portions of the first image and the subsequent images are generated by integrating a grid structure.

6. The method of claim 1, wherein the metadata associated with the selected portion is used to retrieve electronic documents.

7. The method of claim 1, wherein the metadata provides a relationship between the selected portion of the image and the electronic documents that are retrieved.

8. The method of claim 1, further comprising receiving multiple selections of a plurality of segments of the first image.

9. The method of claim 1, wherein retrieving the one or more electronic documents comprises selecting the one or more electronic documents from a plurality of electronic documents based on the selected portion of the image.

10. The method of claim 1, wherein the one or more electronic documents include a patient document, a health document, a medical report, a diagnostic report, a diagnostic image, or any combination thereof.

11. The method according to claim 1, wherein the metadata is a hash tag, a keyword phrase, an index numeral, or any combination thereof.

12. A system for processing electronic documents, the system comprising:
- a processor;
- a memory coupled to the processor, wherein the memory includes instructions executable by the processor to:
  - render an image, wherein the image includes one or more portions;
  - receive a selection event, wherein the selection event includes selection of at least a portion of the image;
  - provide a subsequent image based on the selection event; and
  - retrieve one or more electronic documents corresponding to one or more selection events.

13. The system of claim 12, wherein the instructions are further executable by the processor to assign metadata to the at least one portion of the image.

14. The system of claim 12, wherein the instructions are further executable by the processor to integrate a grid structure with the image.

15. The system of claim 12, wherein the provided subsequent image replaces a previous rendered image.

16. The system of claim 12, wherein the instructions are further executable by the processor to receive one or more selections of the one or more portions of the image.

17. The system of claim 12, wherein the instructions are further executable by the processor to retrieve one or more electronic documents based on metadata associated with the selection event.

18. The system of claim 17, wherein the instructions are further executable by the processor to generate a keyword string based in the metadata associated with the selection event.

19. The system of the claim 17, wherein the instructions are further executable by the processor to generate keyword strings based on the metadata associated with at least a portion of the image and a dictionary archive.

20. The system of claim 14, wherein the one or more electronic documents are stored in a database.

* * * * *